(12) United States Patent
Glossop et al.

(10) Patent No.: US 9,398,892 B2
(45) Date of Patent: Jul. 26, 2016

(54) DEVICE AND METHOD FOR A TRACKABLE ULTRASOUND

(75) Inventors: Neil David Glossop, Toronto (CA); Bradford Johns Wood, Potomac, MD (US)

(73) Assignees: Koninklijke Philips N.V., Eindhoven (NL); THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 2657 days.

(21) Appl. No.: 11/471,629

(22) Filed: Jun. 21, 2006

(65) Prior Publication Data

US 2007/0167787 A1 Jul. 19, 2007

Related U.S. Application Data

(60) Provisional application No. 60/692,271, filed on Jun. 21, 2005.

(51) Int. Cl.
*A61B 8/00* (2006.01)
*A61B 8/12* (2006.01)

(52) U.S. Cl.
CPC ... *A61B 8/00* (2013.01); *A61B 8/12* (2013.01); *A61B 8/445* (2013.01); *A61B 8/58* (2013.01); *A61B 8/4245* (2013.01)

(58) Field of Classification Search
CPC .............................. A61B 8/58; A61B 8/4245
USPC ................. 600/459, 462, 466, 424, 426, 587; 73/1.86
See application file for complete search history.

(56) References Cited

U.S. PATENT DOCUMENTS

| | | | |
|---|---|---|---|
| 3,021,842 A | 2/1962 | Flood | |
| 4,080,706 A | 3/1978 | Heilman et al. | 29/173 |
| 4,279,252 A | 7/1981 | Martin | 128/349 R |
| 4,697,595 A | 10/1987 | Breyer et al. | 128/660 |
| 4,722,056 A | 1/1988 | Roberts et al. | 364/413 |
| 4,777,951 A | 10/1988 | Cribier et al. | 128/344 |

(Continued)

FOREIGN PATENT DOCUMENTS

| | | |
|---|---|---|
| AU | 6367896 | 2/1997 |
| AU | 722539 | 8/2000 |

(Continued)

OTHER PUBLICATIONS

Knaan, Dotan, et al., Effective Intensity-Based 2D/3D Rigid Registration Between Fluoroscopic X-Ray and CT, *MICCAI*, vol. 1, 2003, pp. 351-358.

(Continued)

*Primary Examiner* — Amanda Lauritzen Moher
*Assistant Examiner* — Joseph M Santos Rodriguez

(57) ABSTRACT

The invention provides a method for adjusting the calibration of a tracked ultrasound device using the measured difference between two sets of fiducial markings in two relative positions of a tracker and an scan head of the device. The invention also provides a trackable ultrasound device that enables repeatable attachment of a tracker to a scan head, thus preserving an initial calibration between the tracker and the scan head. Furthermore, the invention provides a calibration jig that can be used to repeatably attach a tracker to an ultrasound scan head or to measure the difference between two relative positions of a tracker and a scan head.

14 Claims, 7 Drawing Sheets

(56) References Cited

U.S. PATENT DOCUMENTS

| | | | | |
|---|---|---|---|---|
| 4,887,606 | A | 12/1989 | Yock et al. | 128/662.05 |
| 4,895,168 | A | 1/1990 | Machek | 128/772 |
| 4,935,019 | A | 6/1990 | Papp, Jr. | 604/362 |
| 4,961,433 | A | 10/1990 | Christian | 128/772 |
| 5,014,708 | A | 5/1991 | Hayashi et al. | 128/653 R |
| 5,042,486 | A | 8/1991 | Pfeiler et al. | 128/653 R |
| 5,045,080 | A | 9/1991 | Dyer et al. | 604/362 |
| 5,085,659 | A | 2/1992 | Rydell | 606/47 |
| 5,116,345 | A | 5/1992 | Jewell et al. | 606/130 |
| 5,187,658 | A | 2/1993 | Cline et al. | 364/413.13 |
| 5,204,625 | A | 4/1993 | Cline et al. | 324/306 |
| 5,207,675 | A | 5/1993 | Canady | 606/40 |
| 5,211,165 | A | 5/1993 | Dumoulin et al. | 128/653.1 |
| 5,221,283 | A | 6/1993 | Chang | 606/130 |
| 5,247,935 | A | 9/1993 | Cline et al. | 128/653.2 |
| 5,251,127 | A | 10/1993 | Raab | 364/413.13 |
| 5,251,635 | A | 10/1993 | Dumoulin et al. | 128/653.2 |
| 5,255,680 | A | 10/1993 | Darrow et al. | 128/653.1 |
| 5,265,610 | A | 11/1993 | Darrow et al. | 128/653.1 |
| 5,271,400 | A | 12/1993 | Dumoulin et al. | 128/653.2 |
| 5,275,165 | A | 1/1994 | Ettinger et al. | 128/653.2 |
| 5,290,266 | A | 3/1994 | Rohling et al. | 604/272 |
| 5,291,010 | A | 3/1994 | Tsuji | 250/208.1 |
| 5,291,890 | A | 3/1994 | Cline et al. | 128/653.2 |
| 5,304,933 | A | 4/1994 | Vavrek et al. | 324/318 |
| 5,305,203 | A | 4/1994 | Raab | 364/413.13 |
| 5,307,812 | A | 5/1994 | Hardy et al. | 128/653.2 |
| 5,318,025 | A | 6/1994 | Dumoulin et al. | 128/653.2 |
| 5,323,779 | A | 6/1994 | Hardy et al. | 128/653.2 |
| 5,327,884 | A | 7/1994 | Hardy et al. | 128/653.2 |
| 5,353,808 | A | 10/1994 | Viera | 128/772 |
| 5,365,927 | A | 11/1994 | Roemer et al. | 128/653.2 |
| 5,368,031 | A | 11/1994 | Cline et al. | 128/653.2 |
| 5,368,032 | A | 11/1994 | Cline et al. | 128/653.2 |
| 5,377,678 | A | 1/1995 | Dumoulin et al. | 128/653.1 |
| 5,383,454 | A | 1/1995 | Bucholz | 128/653.1 |
| 5,383,465 | A | 1/1995 | Lesny et al. | 128/662.05 |
| 5,386,828 | A | 2/1995 | Owens et al. | 128/653.1 |
| 5,389,101 | A | 2/1995 | Heilbrun et al. | 606/130 |
| 5,391,199 | A | 2/1995 | Ben-Haim | 607/122 |
| 5,396,905 | A | 3/1995 | Newman et al. | 128/849 |
| 5,400,383 | A | 3/1995 | Yassa et al. | 378/98.2 |
| 5,437,277 | A | 8/1995 | Dumoulin et al. | 128/653.1 |
| 5,443,066 | A | 8/1995 | Dumoulin et al. | 128/653.1 |
| 5,443,068 | A | 8/1995 | Cline et al. | 128/653.5 |
| 5,445,150 | A | 8/1995 | Dumoulin et al. | 128/653.1 |
| 5,465,732 | A | 11/1995 | Abele | 128/772 |
| 5,480,382 | A | 1/1996 | Hammerslag et al. | 604/95 |
| 5,490,840 | A | 2/1996 | Uzgiris et al. | 604/22 |
| 5,493,598 | A | 2/1996 | Yassa et al. | 378/98.2 |
| 5,526,812 | A | 6/1996 | Dumoulin et al. | 128/653.1 |
| 5,526,814 | A | 6/1996 | Cline et al. | 128/653.2 |
| 5,558,091 | A | 9/1996 | Acker et al. | 128/653.1 |
| 5,603,318 | A | 2/1997 | Heilbrun et al. | 128/630 |
| 5,645,065 | A | 7/1997 | Shapiro et al. | 128/653.1 |
| 5,646,524 | A | 7/1997 | Gilboa | 324/207.17 |
| 5,646,525 | A | 7/1997 | Gilboa | 324/207.17 |
| 5,647,373 | A | 7/1997 | Paltieli | 128/749 |
| 5,705,014 | A | 1/1998 | Schenck et al. | 156/272.4 |
| 5,713,858 | A | 2/1998 | Heruth et al. | 604/93 |
| 5,715,166 | A | 2/1998 | Besl et al. | 364/474.24 |
| 5,715,822 | A | 2/1998 | Watkins et al. | 128/653.5 |
| 5,740,802 | A | 4/1998 | Nafis et al. | 128/653.1 |
| 5,749,835 | A | 5/1998 | Glantz | 600/424 |
| 5,769,790 | A | 6/1998 | Watkins et al. | 600/439 |
| 5,769,861 | A | 6/1998 | Vilsmeier | 606/130 |
| 5,848,969 | A | 12/1998 | Panescu et al. | 600/462 |
| 5,857,032 | A | 1/1999 | Wang et al. | 382/154 |
| 5,868,673 | A | 2/1999 | Vesely | 600/407 |
| 5,873,845 | A | 2/1999 | Cline et al. | 601/3 |
| 5,880,976 | A | 3/1999 | DiGioia, III et al. | 364/578 |
| 5,931,786 | A | 8/1999 | Whitmore, III et al. | 600/459 |
| 5,944,023 | A | 8/1999 | Johnson et al. | 128/899 |
| 5,978,696 | A | 11/1999 | VomLehn et al. | 600/411 |
| 6,016,439 | A | 1/2000 | Acker | 600/411 |
| 6,036,682 | A | 3/2000 | Lange et al. | 604/529 |
| 6,073,043 | A | 6/2000 | Schneider | 600/424 |
| 6,097,978 | A | 8/2000 | Demarais et al. | 600/429 |
| 6,106,476 | A | 8/2000 | Corl et al. | 600/486 |
| 6,141,576 | A | 10/2000 | Littmann et al. | 600/381 |
| 6,147,480 | A | 11/2000 | Osadchy et al. | 324/67 |
| 6,165,184 | A | 12/2000 | Verdura et al. | 606/148 |
| 6,188,355 | B1 | 2/2001 | Gilboa | 342/448 |
| 6,196,980 | B1 | 3/2001 | Akerfeldt et al. | 600/585 |
| 6,203,493 | B1 | 3/2001 | Ben-Haim | 600/117 |
| 6,203,543 | B1 | 3/2001 | Glossop | 606/60 |
| 6,205,411 | B1 | 3/2001 | DiGioia, III et al. | 703/11 |
| 6,210,339 | B1 | 4/2001 | Kiepen et al. | 600/486 |
| 6,216,029 | B1 | 4/2001 | Paltieli | 600/427 |
| 6,226,543 | B1 | 5/2001 | Gilboa et al. | 600/407 |
| 6,233,476 | B1 | 5/2001 | Strommer et al. | 600/424 |
| 6,235,038 | B1 | 5/2001 | Hunter et al. | 606/130 |
| 6,241,690 | B1 | 6/2001 | Burkett et al. | 600/585 |
| 6,266,551 | B1 * | 7/2001 | Osadchy et al. | 600/424 |
| 6,266,552 | B1 | 7/2001 | Slettenmark | 600/424 |
| 6,272,370 | B1 | 8/2001 | Gillies et al. | 600/411 |
| 6,272,371 | B1 | 8/2001 | Shlomo | 600/424 |
| 6,285,898 | B1 | 9/2001 | Ben-Haim | 600/374 |
| 6,285,903 | B1 | 9/2001 | Rosenthal et al. | 600/433 |
| 6,288,785 | B1 | 9/2001 | Frantz et al. | 356/614 |
| 6,308,089 | B1 | 10/2001 | von der Ruhr et al. | 600/338 |
| 6,314,310 | B1 * | 11/2001 | Ben-Haim et al. | 600/424 |
| 6,317,621 | B1 | 11/2001 | Graumann et al. | 600/424 |
| 6,332,089 | B1 | 12/2001 | Acker et al. | 600/424 |
| 6,336,906 | B1 | 1/2002 | Hammarstrom et al. | 600/585 |
| 6,338,716 | B1 * | 1/2002 | Hossack et al. | 600/459 |
| 6,356,783 | B1 | 3/2002 | Hubbard, Jr. | 600/546 |
| 6,380,732 | B1 | 4/2002 | Gilboa | 324/207.17 |
| 6,381,485 | B1 | 4/2002 | Hunter et al. | 600/407 |
| 6,383,174 | B1 | 5/2002 | Eder | 606/1 |
| 6,385,482 | B1 | 5/2002 | Boksberger et al. | 600/424 |
| 6,427,079 | B1 | 7/2002 | Schneider et al. | 600/424 |
| 6,442,417 | B1 | 8/2002 | Shahidi et al. | 600/429 |
| 6,453,190 | B1 * | 9/2002 | Acker et al. | 600/424 |
| 6,468,265 | B1 | 10/2002 | Evans et al. | 606/1 |
| 6,473,635 | B1 | 10/2002 | Rasche | 600/428 |
| 6,484,118 | B1 | 11/2002 | Govari | 702/150 |
| 6,493,589 | B1 | 12/2002 | Medhkour et al. | 607/99 |
| 6,498,944 | B1 | 12/2002 | Ben-Haim et al. | 600/407 |
| 6,499,488 | B1 | 12/2002 | Hunter et al. | 128/899 |
| 6,500,114 | B1 | 12/2002 | Petitto et al. | 600/156 |
| 6,512,958 | B1 | 1/2003 | Swoyer et al. | 607/117 |
| 6,529,758 | B2 | 3/2003 | Shahidi | 600/407 |
| 6,547,782 | B1 | 4/2003 | Taylor | 606/14 |
| 6,558,333 | B2 | 5/2003 | Gilboa et al. | 600/466 |
| 6,574,492 | B1 | 6/2003 | Ben-Haim et al. | 600/374 |
| 6,574,498 | B1 | 6/2003 | Gilboa | 600/424 |
| 6,580,938 | B1 | 6/2003 | Acker | 600/424 |
| 6,585,654 | B2 | 7/2003 | White et al. | 600/463 |
| 6,588,333 | B1 | 7/2003 | Homer et al. | 101/32 |
| 6,591,129 | B1 | 7/2003 | Ben-Haim et al. | 600/424 |
| 6,593,127 | B1 | 7/2003 | McKinnon | 600/411 |
| 6,593,884 | B1 | 7/2003 | Gilboa et al. | 342/448 |
| 6,615,155 | B2 | 9/2003 | Gilboa | 702/150 |
| 6,619,838 | B2 | 9/2003 | Bencini et al. | 378/190 |
| 6,628,987 | B1 | 9/2003 | Hill et al. | 607/9 |
| 6,690,963 | B2 | 2/2004 | Ben-Haim et al. | 600/424 |
| 6,702,780 | B1 | 3/2004 | Gilboa et al. | 604/95.04 |
| 6,711,429 | B1 | 3/2004 | Gilboa et al. | 600/407 |
| 6,719,700 | B1 | 4/2004 | Willis | 600/462 |
| 6,735,471 | B2 | 5/2004 | Hill et al. | 607/2 |
| 6,748,112 | B1 | 6/2004 | Nguyen et al. | 382/203 |
| 6,753,873 | B2 | 6/2004 | Dixon et al. | 345/542 |
| 6,782,287 | B2 | 8/2004 | Grzeszczuk et al. | 600/424 |
| 6,783,536 | B2 | 8/2004 | Vilsmeier et al. | 606/130 |
| 6,785,571 | B2 | 8/2004 | Glossop | 600/424 |
| 6,788,967 | B2 | 9/2004 | Ben-Haim et al. | 600/424 |
| 6,792,303 | B2 | 9/2004 | Taimisto | 600/424 |
| 6,893,429 | B2 | 5/2005 | Petersen | 604/537 |
| 6,895,268 | B1 | 5/2005 | Rahn et al. | 600/429 |
| 6,916,290 | B2 | 7/2005 | Hedengren et al. | 600/549 |
| 7,085,400 | B1 | 8/2006 | Holsing et al. | 382/103 |
| 7,386,339 | B2 | 6/2008 | Strommer et al. | 600/424 |
| 7,570,791 | B2 | 8/2009 | Frank et al. | 382/132 |

(56) References Cited

U.S. PATENT DOCUMENTS

| | | | |
|---|---|---|---|
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0087101 A1* | 7/2002 | Barrick et al. | 600/587 |
| 2002/0143317 A1 | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165448 A1 | 11/2002 | Ben-Haim et al. | 600/424 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0074011 A1 | 4/2003 | Gilboa et al. | 606/130 |
| 2003/0092988 A1 | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1 | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1 | 11/2004 | Miller | 128/207.14 |
| 2004/0234933 A1 | 11/2004 | Dawson et al. | 434/262 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0049520 A1 | 3/2005 | Nakao | 600/562 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0113659 A1* | 5/2005 | Pothier et al. | 600/372 |
| 2005/0182295 A1 | 8/2005 | Soper et al. | 600/117 |
| 2005/0182319 A1 | 8/2005 | Glossop | 600/424 |
| 2005/0228270 A1 | 10/2005 | Lloyd et al. | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| BR | 9609484 | 12/1999 |
| CA | 2226938 | 2/1997 |
| DE | 69420228 D | 9/1999 |
| DE | 69420228 T | 4/2000 |
| DE | 19845267 C1 | 5/2000 |
| EP | 0 845 959 | 6/1998 |
| EP | 0 654 244 | 8/1999 |
| EP | 1 466 552 | 10/2004 |
| IL | 0107523 | 1/2000 |
| IL | 0114610 | 7/2000 |
| JP | 10-277047 | 10/1998 |
| JP | 2000500031 T | 1/2000 |
| JP | 2005152463 | 6/2005 |
| WO | WO 97/03609 | 2/1997 |
| WO | WO 98/56295 | 12/1998 |
| WO | WO 00/22904 | 4/2000 |

OTHER PUBLICATIONS

Gee, A. H., et al., "3D Ultrasound Probe Calibration Without a Position Sensor", CUED/F-INFENG/TR 488, University of Cambridge, Department of Engineering, Sep. 2004, 21 pages.

Lindseth, Frank, et al., "Probe Calibration for Freehand 3D Ultrasound Reconstruction and Surgical Navigation", Dec. 2002, 27 pages.

Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep 22-25, 1996).].

Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

RITA StarBurst Soft Tissue Access System and RITA StarBurst Hard Tissue Access System, http://www.ritamedical.com, Rita Medical Systems, Inc., copyright 2002, 8 pages.

Cool-tip RF Tissue Ablation System, Cool-tip RF System, and Cool-tip Electrodes, http://www.valleylab.com/static/cooltip/products.html, Valleylab, copyright 2004, 4 pages.

LeVeen Needle Electrode, Boston Scientific, printed from http://www.bostonscientific.com/med_specialty/deviceDetail.ihtml?task=tskBasicDevice . . . , printed on Sep. 13, 2004, 1 page.

Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

Tanase, Dafina, et al., "Magnetic Sensors for Use on Guide Wires or Catheters", in *SeSens* 2001, in press 2002, pp. 868-872.

Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

Solomon, Stephen B., et al., "Real-Time Cardiac Catheter Navigation on Three-Dimensional CT Images", *Journal of Interventional Cardiac Electrophysiology*, vol. 8, 2003, pp. 27-36.

Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

Baert, Shirley A. M., et al., "Endpoint Localization in Guide Wire Tracking During Endovascular Interventions", *Academic Radiology*, vol. 10, No. 12, Dec. 2003, pp. 1424-1432.

Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

(56) References Cited

OTHER PUBLICATIONS

Baert, Shirley A. M., et al., "Guide-Wire Tracking During Endovascular Interventions", *IEEE Transactions on Medical Imaging*, vol. 22, No. 8, Aug. 2003, pp. 965-972.

Kobashi, Keiji, et al., "A New Biomechanical Model Based Approach on Brain Shift Compensation", *MICCAI 2003*, LNCS 2878, 2003, pp. 59-66.

Timinger, Holger, et al., "Motion Compensation for Interventional Navigation on 3D Static Roadmaps Based on an Affine Model and Gating", *Physics in Medicine and Biology*, vol. 49, 2004, pp. 719-732.

Lorigo, Liana M., et al., "Curves: Curve Evolution for Vessel Segmentation" *Medical Image Analysis*, vol. 5, 2001, pp. 195-206 (pp. 1-14).

Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.

Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.

"Semi-Automatic Registration for Image Guided Surgery", Traxtal poster presented at CAOS '99 (Computer Assisted Orthopaedic Surgery, 4$^{th}$ International Symposium), MICCAI, Mar. 17-19, 1999, Davos, Switzerland, 1 page.

Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.

Livyatan, Harel, "Calibration and Gradient-Based Rigid Registration of Fluoroscopic X-raysto CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.

SuperDimension, Ltd, web page, updated in Sep. 2005, 1 page.

Schweikard, Achim, et al., "Robotic Motion Compensation for Respiratory Movement During Radiosurgery", *Computer Aided Surgery*, vol. 5, 2000, pp. 263-277.

Solomon, Stephen B., et al., "Real-Time Bronchoscope Tip Localization Enables Three-Dimensional CT Image Guidance for Transbronchial Needle Aspiration in Swine" *Chest*, vol. 114, No. 5, Nov. 1998, pp. 1405-1410.

Ellsmere, James, et al., "A Navigation System for Augmenting Laparoscopic Ultrasound", Center for Integration of Medicine and Innovative Technology, Cambridge, Massachusetts, 8 pages.

Hofstetter, R., et al., "Fluoroscopy Based Surgical Navigation—Concept and Clinical Applications", Maurice E. Muller Institute for Biomechanics, University of Bern, Switzerland, 1997, 3 pages.

Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

Summers, Ronald M., et al., "Colonic Polyps: Complementary Role of Computer-Aided Detection in CT Colonography", *Radiology*, vol. 225, No. 2, Nov. 2002, pp. 391-399.

Hara, A. K., et al., "Reducing Data Size and Radiation Dose for CT Colonography", *AJR*, vol. 168, May 1997, pp. 1181-1184.

\* cited by examiner

DEVICE AND METHOD FOR A TRACKABLE ULTRASOUND

REFERENCE TO RELATED APPLICATIONS

This application claims priority to U.S. Provisional Patent Application No. 60/692,271, filed Jun. 21, 2005, which is hereby incorporated by reference herein in its entirety.

STATEMENT REGARDING FEDERALLY SPONSORED RESEARCH AND DEVELOPMENT

This invention may be supported by the Department of Health and Human Services. The Government of the United States of America may have certain rights in the invention disclosed and claimed below.

FIELD OF THE INVENTION

The invention provides a device and method for tracking an ultrasound.

BACKGROUND

Ultrasound devices typically include an ultrasonic transducer with scan/receive heads, a processing unit, and a display device. Ultrasonic transducers may be adapted for special applications such as, for example, transcutaneous applications, laparoscopic applications, transrectal applications, endo-cavity probes, vaginal probes, 2D and 3D phased array probes, and/or other probes or applications. Laparoscopic ultrasound devices typically include an ultrasonic transducer with a movable scan head, a handle, and an apparatus for controlling the orientation of the scan head. An image-guided ultrasound device makes use of sensor elements or position indicating elements placed into the head of the ultrasound transducer and a companion tracking device that can determine the position and/or orientation of sensor elements in the coordinate system of the tracking device. After calibrating the sensor elements to the scan plane of the ultrasonic transducer, the position and/or orientation of the scan plane can also be determined. Using registration techniques, position and orientation information regarding the scan plane of the ultrasound device enables merging and integration of live ultrasound images to preoperative scans (e.g., computerized tomography [CT] scans, magnetic resonance [MR] scans, or other images). Information regarding registration of position/orientation data to image/scan data, production of merged or integrated images therefrom, and/or other information useful with the invention may be found in U.S. patent application Ser. No. 11/059,336 (U.S. Patent Publication No. 2005/0182319), entitled "Method and Apparatus for Registration, Verification, and Referencing of Internal Organs," which is hereby incorporated by reference herein in its entirety.

Attachment of one or more electromagnetically tracked sensor elements to an ultrasound such as, for example, a laparoscopic ultrasound, may offer a number of advantages over the state of the art in trackable ultrasound devices. For example, the scan plane of an ultrasonic transducer can be tracked within the patient's body (as opposed to optical tracking, which is limited to line-of-sight applications) for the aforementioned purpose of superimposing ultrasound images to preoperative images. In addition, it would be advantageous to utilize devices and methods that do not require constant recalibration of the sensor elements with the scan plane in situations where the relative positions of the sensor elements and the ultrasound transducer are changed after initial calibration. By placing a sensor element adjacent to the transducer of an ultrasound device, the device is intrinsically more accurate because the "lever effect" caused when the sensor is located far from the transducer is minimized. The "lever effect" causes a small error in angular measurement by the sensor element to appear as a large error in the position of the transducer.

SUMMARY OF THE INVENTION

In one embodiment, the invention provides a trackable ultrasound device such as, for example, a trackable laparoscopic ultrasound device, that may be used to produce merged images of preoperative scans and interoperative ultrasound images. In one embodiment, the trackable ultrasound device includes an ultrasonic transducer that generates an image of material existing along its scan plane. The trackable ultrasound device also includes a tracker, which is affixed to or near the ultrasonic transducer such that the tracker moves along with any movable parts of a scan head to which the ultrasonic transducer is attached. As affixed in this manner, the tracker enables the determination of the location, direction, and/or orientation of the scan plane even when the ultrasonic transducer moves relative to other parts of the ultrasound device.

In one embodiment, the ultrasonic transducer may include features that allow mating of the tracker to the scan head. Such features may include but are not limited to machined grooves, keyways, divots, alignment pins, spring-loaded balls to engage holes, alignment marks, or other features. These features may allow repeatable and accurate alignment and realignment of the tracker with the scan head.

In one embodiment, the ultrasound device may include fiducials (also referred to herein as "fiducial markings"). These fiducials may include divots, indicator markings, ball bearings, or other elements that are visible under one or more imaging modalities. These fiducials may provide point and/or path references, wherein a reference path can include a plurality of points provided by multiple fiducials. In one embodiment, the position of these fiducials may be sampled using a tracked pointer. In one embodiment, the fiducials may be visible on one or more imaging modalities such as, for example, an x-ray device or other imaging modality. The fiducials may be present on the ultrasound transducer/scan head, the tracker, or other part of the ultrasound device.

The tracker may also include one or more sensor elements. The sensor elements may include electromagnetic sensor coils or other position indicating elements that can be used to indicate position and/or orientation relative to a tracking device. In some embodiments, if two or more sensor elements are used, they can be placed at a known angle relative to one another, thereby providing a perspective indication of depth.

As mentioned above, the tracker includes a plurality of fiducials (e.g., "tracker fiducial markings"). In general, the tracker fiducial markings are in a fixed and known spatial relationship with the sensor elements of the tracker. Accordingly, the fiducials on the scan head (e.g., scan head fiducial markings or transducer fiducial markings) are in a fixed and known spatial relationship with the scan plane of the ultrasonic transducer.

In one embodiment, the invention provides for the prevention of relative movement between the tracker and the ultrasonic transducer by using alignment and engaging features (e.g., alignment elements) on the scan head, the tracker, and/or other parts of the device. This prevents the need for recalibration of the tracker to the ultrasonic transducer. For example, the alignment and engaging features enable the tracker to be removed and reliably replaced onto the scan head in the same position, while preserving an initial calibration (i.e., because the alignment features ensure that the relative positions of the tracker and the ultrasonic transducer remain the same).

In another embodiment, movement of the tracker relative to the ultrasonic transducer can be prevented by using the alignment and engaging features on the scan head, the tracker, and/or other portions of the ultrasound device to engage special jigs, thus eliminating the necessity of recalibration.

In one embodiment, if relative movement between the tracker and the ultrasonic transducer does occur after initial calibration (e.g., either by intentional remounting or for other reasons), the invention provides a method for adjusting the initial calibration, thus avoiding a time-consuming and/or difficult recalibration. This calibration adjustment method compensates for the relative movement between the tracker and the ultrasonic transducer using the tracker fiducial markings and the scan head fiducial markings.

In one embodiment, the initial calibration maybe performed. In this initial calibration, the scan plane of the ultrasonic transducer may be calibrated relative to (or brought into coincidence with) the coordinate system of the tracker. This may be done using methods known in the art and may result in the calculation of an initial calibration transformation matrix $T_{ts}$.

In one embodiment, the tracker fiducial markings and the scan head fiducial markings may then be sampled in the same frame of reference (e.g., using a tracked probe, imaging modality, or other method) and used to obtain primary transformation matrix $T_{tu}$.

The calibrated system may then be used. This use may be in a clinical application or may include a test use. In any event, the initial calibration transformation matrix $T_{ts}$ is employed to determine the scan plane of the ultrasonic transducer from sampled data of the sensor elements of the tracker. As mentioned herein, this determination allows preoperative images to be merged with interoperative ultrasound data.

In one embodiment, the tracker may then be removed from the ultrasound device and replaced in a different position relative to the ultrasonic transducer. The tracker fiducial markings and the scan head fiducial markings are again sampled (e.g., using a tracked probe, imaging modality, or other method) and used to calculate a secondary transformation matrix $T'_{tu}$ between the scan head and the tracker.

A differential transformation matrix T is then calculated between $T_{tu}$ (the primary transformation matrix) and $T'_{tu}$ (the secondary transformation matrix). The differential transformation matrix represents the difference between the first and second relative positions of the tracker and the ultrasonic transducer/scan head. Because the spatial relationships between the sensor elements and the scan plane are known relative to their respective fiducial markings (e.g., the tracker fiducial markings and the scan head fiducial markings) the differential transformation matrix provides an accurate representation of how to adjust the initial calibration.

Accordingly, the initial calibration is adjusted and the trackable laparoscopic ultrasound device can be used without recalibration.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DESCRIPTION OF THE INVENTION

Figure 1:
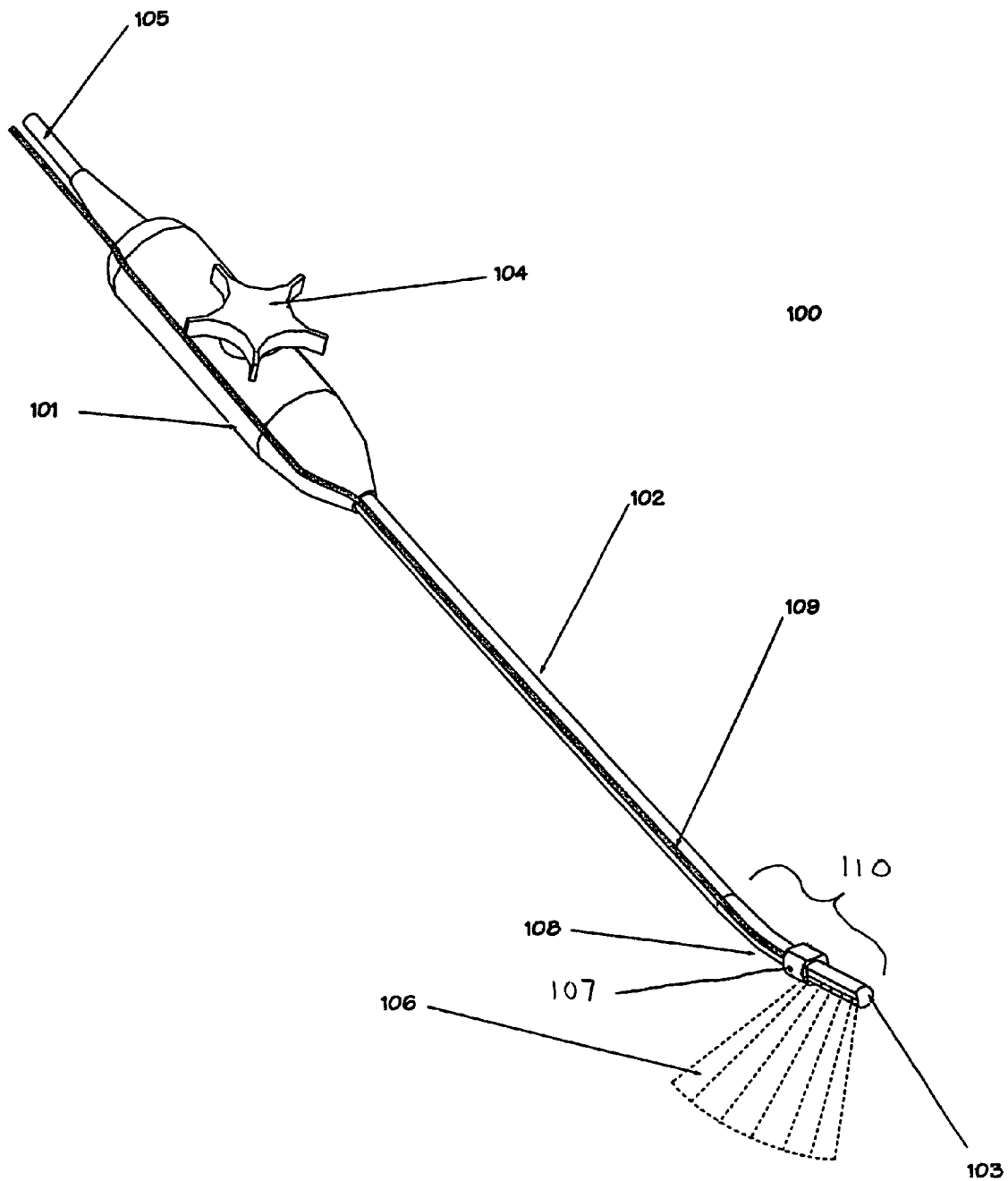
FIG. 1 Illustrates a trackable laparoscopic ultrasound device, according to an embodiment of the invention.

In one embodiment, the invention provides a device for tracking the ultrasonic transducer of an ultrasound device such as, for example, a trackable laparoscopic ultrasound device. FIG. 1 illustrates a trackable laparoscopic ultrasound device 100 according to an embodiment of the invention. In one embodiment, ultrasound device 100 includes a handle 101, an elongated shaft 102, a scan head 110, a control handle 104, a tracker 107, and/or other elements. Control handle 104 controls the pointing direction of a scan head 110, which includes an ultrasonic transducer 103.

Signals are sent to and from ultrasonic transducer 103 via cable 105, which may be routed through the interior of handle 101 and elongated shaft 102. In other embodiments, cable 105 may be routed or located elsewhere.

Trackable laparoscopic ultrasound device 100 is designed to generate an image of material existing along a scan plane 106, which extends from ultrasonic transducer 103. In one embodiments, more than one scan plane may originate from ultrasonic transducer 103.

Trackable laparoscopic ultrasound device 100 also includes a tracker 107, which is affixed to or near ultrasonic transducer 103 at a location 108 such that tracker 107 moves along with any movable parts of scan head 110 such as, for example, an articulating (movable) section of scan head 110, ultrasonic transducer 103, or other movable part. As affixed in this manner, tracker 107 enables the determination of the location, direction, and/or orientation of scan plane 106 even when ultrasonic transducer 103 moves relative to elongated shaft 102 or other parts of ultrasound device 100. This eliminates the need for encoders or other devices to measure the location of the transducer. In one embodiment, cable 109 routes signals from tracker 107 to control equipment (e.g., a tracking device, a computer-implemented control unit, and/or other device) that determines the position and orientation of tracker 107/ultrasonic transducer 103.

Figure 2:
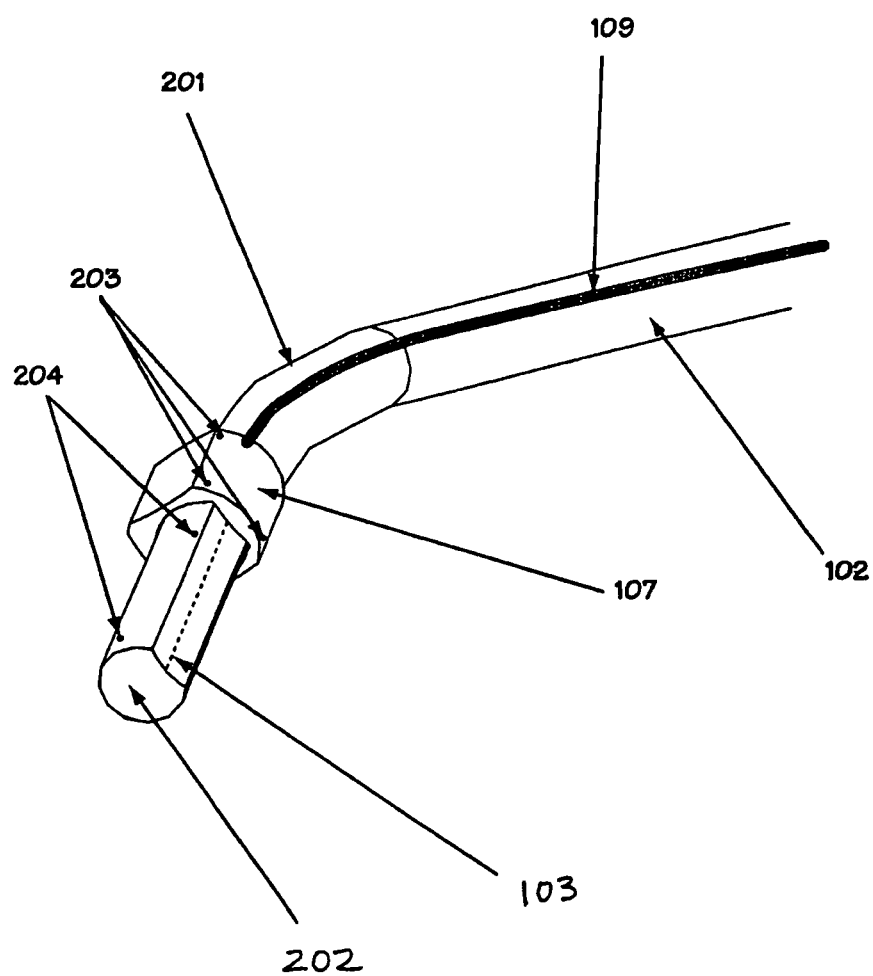
FIG. 2 Illustrates a close-up of a scan head of a trackable laparoscopic ultrasound device, according to an embodiment of the invention.

FIG. 2 illustrates a close-up of scan head 110 of trackable ultrasound device 100. In one embodiment, elongated shaft 102 may be connected to articulating section 201. Articulating section 201 may allow ultrasonic transducer 103 to be moved in multiple directions relative to shaft 102 such as left-right and forward-back. It may allow also combinational motions (e.g., left and back). Generally, such motion may be effected, for example, through the use of one or more steering wires attached to the control handle(s) 104 of FIG. 1 through shaft 102.

As mentioned above, tracker 107 may be fixed to ultrasound device 100 such that tracker 107 moves with ultrasonic transducer 103. As such, tracker 107 may be fixed to an articulating shaft 202 that includes ultrasonic transducer 103. In one embodiment, tracker 107 may be placed in a location that does not overlap ultrasonic transducer 103.

Any electrical connections (e.g., signal carrying leadwires, etc.) required by tracker 107 may be provided by cable 109.

In one embodiment, ultrasonic transducer 103 may include features (e.g., alignment elements) that allow mating of tracker 107 to scan head 110 (e.g., to part of articulating shaft 201 or other part of scan head 110 that enables tracker 107 to move with ultrasonic transducer 103). Such features may include but are not limited to machined grooves, keyways, divots, alignment pins, spring-loaded balls to engage holes, alignment marks, or other features. Tracker 107 may include corresponding/mating alignment elements machined into its body to allow repeatable and accurate alignment and realignment of tracker 107 with scan head 110.

In one embodiment, alignment elements may be present on both the scan head 110 and the tracker 107, and may allow engagement and temporary fixation of external jigs. The jigs may enable precise, reproducible alignment to be performed between tracker 107 and scan head 110. The jigs may alternately provide a way to measure the alignment of scan head 110 and tracker 107 (or changes therein between first and second positions). One such jig may engage scan head 110. Another part of the jig or a separate jig may engage tracker 107. In one embodiment, the jig or jigs may be equipped with protrusions, "wings," or extensions that may engage either tracker 107 or the scan head 110. These wings may provide a way of assisting the alignment or clamping of tracker 107 or scan head 110, and may optionally contain fiducials, divots, sensor elements, or paths. The wings may provide a "leverarm effect" enabling more precise relative rotational alignment or measurement of the relative positions of tracker 107 and ultrasonic transducer 103 that might otherwise be possible using features on the devices themselves. Details of an embodiment of a calibration jig are included in FIG. 6, which is discussed in detail below.

In one embodiment, trackable laparoscopic ultrasound device 100 may contain fiducials (also referred to herein as "fiducial markings"). Fiducials may include divots, indicator markings, ball bearings, or other elements. These fiducials may provide point and/or path references, wherein a reference path can include a plurality of points provided by multiple fiducials. In one embodiment, the position of these fiducials may be sampled using a tracked pointer. In one embodiment, the fiducials may be visible on one or more imaging modalities such as, for example, an x-ray device or other imaging modality. The fiducials may be present on ultrasonic transducer 103, tracker 107, or other part of ultrasound device 100. FIG. 2 illustrates tracker fiducials 203 on tracker 207 and transducer or scan head fiducials 204 on ultrasonic transducer 103.

Figure 3:
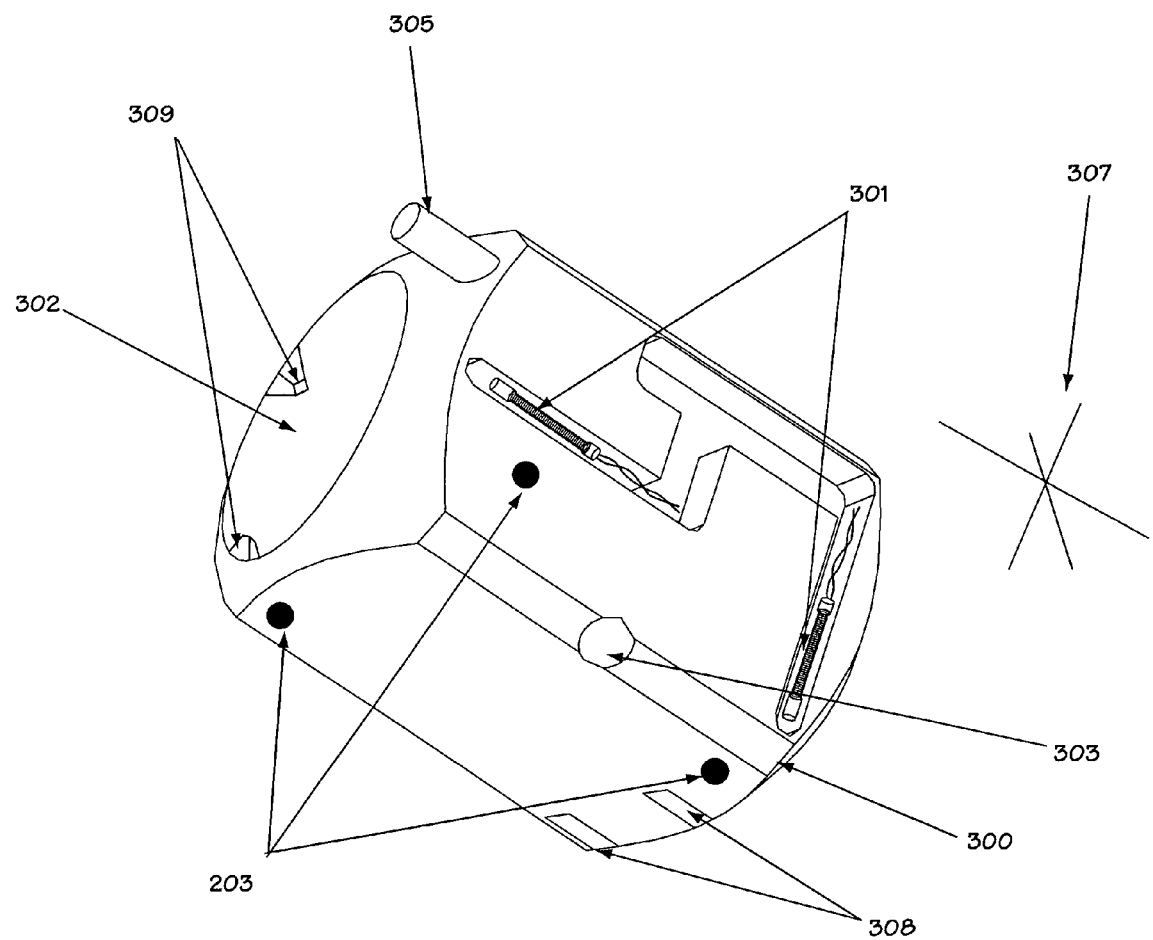
FIG. 3 Illustrates a tracker for use with a trackable laparoscopic ultrasound device, according to an embodiment of the invention.

FIG. 3 illustrates a close-up of tracker 107. Tracker 107 may include a housing 300. In one embodiment, housing 300 may be made of a plastic material. In other embodiments, housing 300 may be made of metals, composites, a combination of plastic and metal, or other materials. In designs that use electromagnetic tracking devices, plastic may be preferred since metals are sometimes particularly good conductors that may offer circular current paths enabling eddy currents that distort the electromagnetic field measurements and thereby diminish the accuracy of the tracking device.

Housing 300 can be mounted to trackable laparoscopic ultrasound device 100 by threading it over scan head 110 using mounting hole 302. Housing 300 can then be secured to ultrasound device 100 using mounting element 303. In some embodiments, mounting element 303 may include, for example, a band, a screw, clips that elastically engage features on scan head 110, or other restraining element or fastener. In some embodiments, multiple mounting elements may be used.

In some embodiments, housing 300 may include alignment elements 308 and/or 309 that enable repeatable placement of tracker 107 on ultrasound transducer 103.

In one embodiment, one or more sensor elements 301 may be attached to housing 300. Sensor elements 301 may include electromagnetic sensor coils, optical devices, inertial measurement systems, or other position indicating elements that can be used to indicate position and/or orientation relative to a tracking device. In some embodiments, tracker 107 may include one sensor element 301 that is a 6 degree of freedom sensor element. In other embodiments, tracker 107 may include two or more 4 or 5 degree of freedom sensor elements 301 (as illustrated in FIG. 3) or three 3 degree of freedom elements. In some embodiments, if two or more sensor elements 301 are used, they can be placed at a known angle relative to one another such as, for example, perpendicular to one another (as illustrated in FIG. 3), thereby providing a method of determining all 6 degrees of freedom. In another embodiment, multiple sensor elements 301 may be arranged in parallel.

Any sensor wires used with sensor elements 301 may be connected to their respective sensor elements 301 and may exit tracker 107 at position 305 (position 305 may comprise a portion of cable 109). If wireless sensor elements 301 are used, wiring may not be needed. Sensor elements 301 may be rigidly affixed to housing 300 using adhesive such as, for example, epoxy and, as illustrated in FIG. 3, may also be recessed within housing 300.

As mentioned above, tracker 107 can also further include a plurality of tracker fiducials 203. In general, tracker fiducials 203, are in a position known and fixed relative to sensor elements 301 in a coordinate system 307 that is the coordinate system of sensor elements 301 and their corresponding tracking device.

In one embodiment, tracker 107 contains machined features such as notches, prominences, marks, or other alignment elements 308 or 309 for engaging corresponding/mating alignment elements on trackable laparoscopic ultrasound device 100. In one embodiment, the notches or alignment elements 308 and 309 are used for engaging an external jig that is mounted to tracker 107. In one embodiment, tracker fiducials 203 may also be used for this purpose. The jig used may be mounted to trackable laparoscopic ultrasound device 100 using notches or other similar features on ultrasound transducer 103.

In one embodiment, a jig used in this manner may be insertable through laparoscopic ports (e.g., 12 mm ports, 5 mm ports, or other ports) such that an internal endocavitary calibration may be performed. This internal endocavitary calibration may be used to correct for minor inhomogeneities at the site of use. Additionally, the presence of a computerized tomography (CT) scanner during use (e.g., in the operating room) may necessitate the presence of internal fiducials on the jig, tracker 107, or the patient. In one embodiment, fiducials internal to a patient may include curved needles or other elements.

Prior to use with a patient, tracker 107 is placed onto/attached to a laparoscopic ultrasound device (thus forming a trackable laparoscopic ultrasound device, the same as or similar to device 100). The device must then be calibrated to relate the coordinate system of tracker 107 (e.g., coordinate system 307 of FIG. 3) to the coordinate system of the scan plane of ultrasonic transducer 103 (e.g., scan plane 106). Many methods of calibration exist, some of which are summarized in the document "3D ULTRASOUND PROBE CALIBRATION WITHOUT A POSITION SENSOR" by A. H. Gee, N. E. Houghton, G. M. Treece and R. W. Prager CUED/F-INFENG/TR 488 September 2004 (Cambridge University, Department of Engineering, Trumpington Street, Cambridge CB2 1PZ, United Kingdom) and in the document "F. Lindseth, G. A. Tangen, T. Lango, and J. Bang. Probe calibration for freehand 3-D ultrasound. Ultrasound in Medicine and Biology, 29(11): 1607-1623, November 2003," both of which are hereby incorporated by reference herein in their entirety. Typically, this initial calibration can be difficult and/or time consuming.

Figure 5:
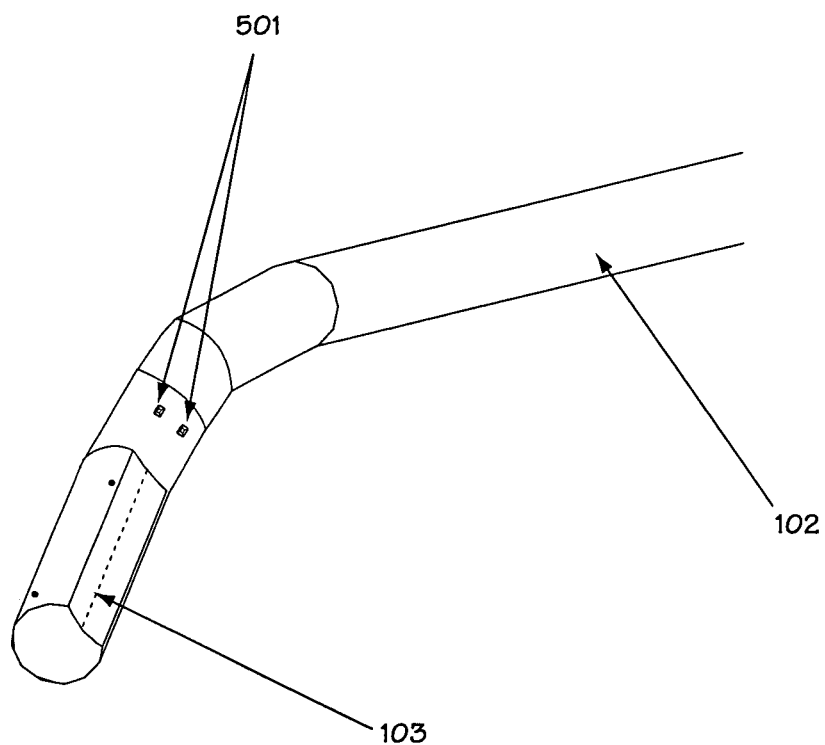
FIG. 5 illustrates a close-up of a scan head of a trackable laparoscopic ultrasound device, according to an embodiment of the invention.

Any subsequent movement of tracker 107 relative to the ultrasonic transducer will normally necessitate another time-consuming recalibration prior to use. However, the present invention overcomes the need for this time-consuming recalibration. In one embodiment, the invention provides for the prevention of relative movement between tracker 107 and ultrasonic transducer 103 by using alignment and engaging features (e.g., alignment elements 308, 309, 501, etc.) on scan head 110 and tracker 107. This prevents the need for recalibration of tracker 107 to ultrasonic transducer 103. For example, the alignment elements 308 and 309 enable tracker 107 to be removed and reliably replaced onto scan head 110 in the same position, while preserving an initial calibration (e.g., because the alignment elements ensure that the relative positions of tracker 107 and ultrasonic transducer 103 remain the same). In one embodiment, the alignment elements on tracker 107 mate with corresponding alignment elements 501 present on scan head 110 (illustrated in FIG. 5) to ensure reproducible mounting of tracker 107 to scan head 110. These alignment elements are shown as alignment pegs and holes, but may be notches, grooves, clips, or other elements that are able to assist in positioning and retaining the relative alignment of tracker 107 with ultrasound 103.

In one embodiment, tracker 107 itself may comprise female receiver "ring" (see, for example, mounting hole 302 of FIG. 3) that is attached over a male portion of ultrasonic transducer 103 onto a specific area of scan head 110. Insertion the tracker ring fully onto ultrasonic transducer 103 may result in the tracker ring coming to rest in a predefined position that has a predefined offset and distance from the tip of ultrasonic transducer 103. Alignment elements may removably secure tracker ring to scan head 110. For example, alignment elements 309 may removably mate with corresponding alignment elements 501 on scan head 110.

In another embodiment (which may be used in conjunction with other methods to serve as a "check" or verification that the system is accurate), the necessity of recalibration following movement of tracker 107 relative to ultrasonic transducer 103 can be prevented by using the alignment and engaging features on scan head 110 (e.g., alignment elements 501), tracker 107 (e.g., alignment elements 508 and 509), and/or other portions of ultrasound device 100 to engage special jigs. In one embodiment, the jigs may be of large dimensions, may enable the relative positions and rotations of tracker 107 relative to ultrasonic transducer 103 to be carefully adjusted since the lever arm effect exaggerates the relative positions. In one embodiment, fiducials and/or sensor elements may be placed on the aforementioned jigs, if used.

In one embodiment, if relative movement between tracker 107 and ultrasonic transducer 103 does occur after initial calibration (e.g., either by intentional remounting or for other reasons), the invention provides a method for adjusting the initial calibration, thus avoiding a time-consuming and/or difficult recalibration. This calibration adjustment method compensates for the relative movement between tracker 107 and ultrasonic transducer 103 using tracker fiducials 203 and scan head fiducials 204. As mentioned above, this method may be used in conjunction with other methods to serve as a "check" that the system is accurate.

Figure 4:
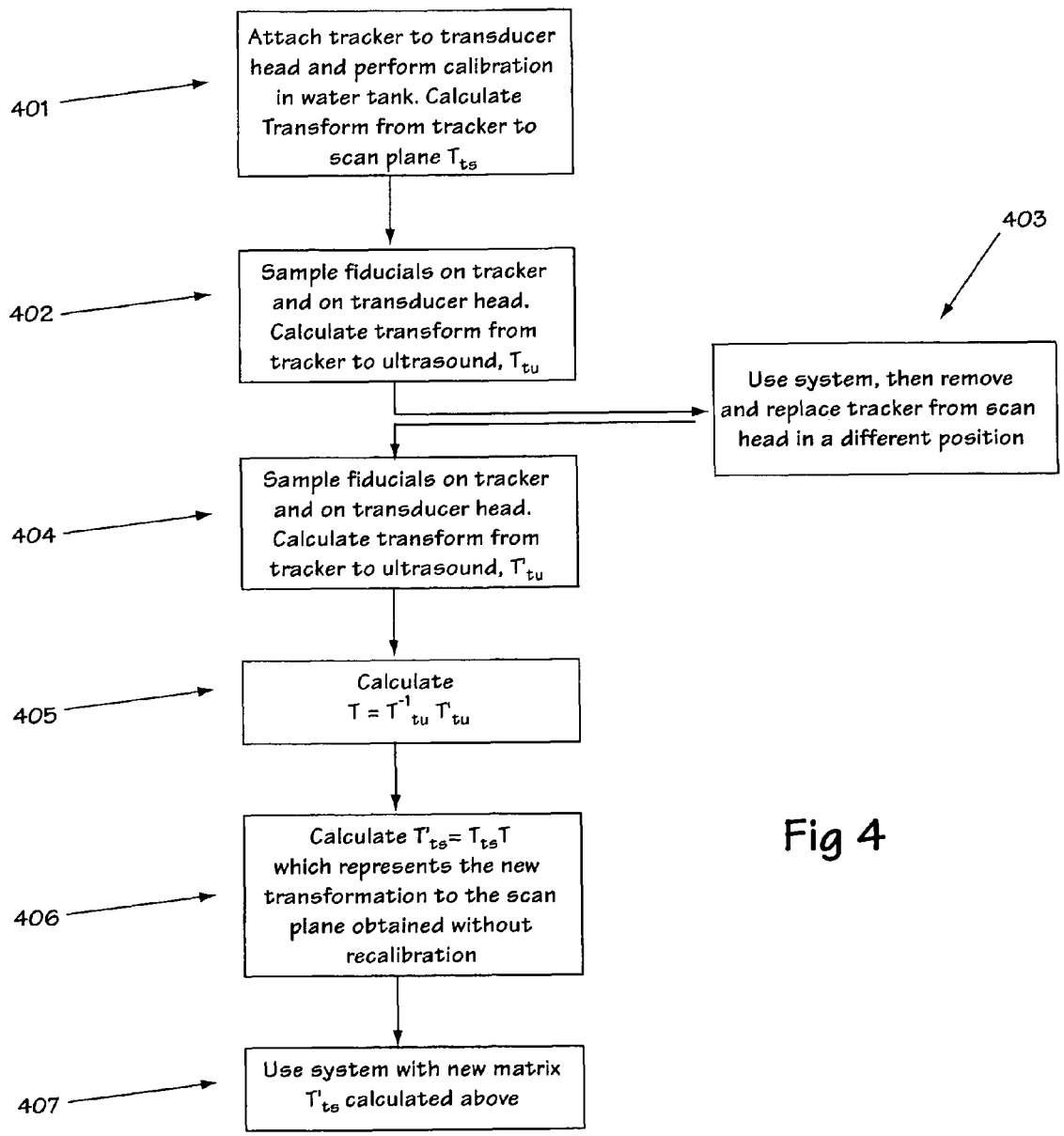
FIG. 4 illustrates a process for adjusting an initial calibration of a tracker to a scan plane in a trackable ultrasound device, according to an embodiment of the invention.

FIG. 4 illustrates a process 400 for adjusting an initial calibration of a trackable laparoscopic ultrasound device (e.g., device 100) after relative movement between a tracker element (e.g., tracker 107) and an ultrasonic transducer (e.g., ultrasonic transducer 103). In an operation 401, the initial calibration maybe performed. In this initial calibration, scan plane 106 of ultrasonic transducer 103 may be calibrated relative to (or brought into coincidence with) the coordinate system of tracker 107. This may be done, for example, using the methods of Gee et al. and/or Lindseth et al., or using other methods known in the art.

In performing the calibration, at least three calibration locations are sampled on using the sensor elements (sensor elements 103) of tracker 107. The same three calibration locations may then be sampled using scan plane 106 of ultrasonic transducer 103. The resultant data may be considered initial calibration sample data and may be used to calculate an initial calibration transformation matrix $T_{ts}$. Transformation matrix $T_{ts}$ relates the coordinate system of the scan plane 106 of ultrasonic transducer 103 with the coordinate system of tracker 107 and represents the rigid transformation between the scan plane 106 and the reported position and orientation of tracker 107. Since the initial calibration relates tracker 107's coordinate system with that of scan plane 106 of ultrasonic transducer 103, the calibration can be calculated for any positioning of tracker 107 onto scan head 110 once the relative position between tracker 107 and ultrasonic transducer 103 is known in the calibrated situation.

In one embodiment, the initial calibration of operation 401 may take place in a water tank as described in Gee et al. and Lindseth et al. The water tank is normally used to assist in the propagation of the sound waves which otherwise are attenuated in air. Typically, such a calibration takes the form of measurements of the location of several points in the water tank (formed, for example, by the intersection of crossed wires suspended in the tank) with the ultrasound in the coordinate system of the scan plane of the ultrasound and determining the location of the same points in space of the position sensor.

In an operation 402, fiducials on both tracker 107 (e.g., tracker fiducials 203) and ultrasonic transducer 103 (e.g., scan head fiducials 204) may then be sampled in the same frame of reference. A calculation relating the coordinate system of tracker 107 to the coordinate system of scan head 110 (and thus to scan plane 106) may then be performed using a method such as the iterative closest point (ICP), singular valued decomposition (SVD) technique, or other technique to determine a primary transformation matrix. Sampling of these fiducials may be performed using, for example, a tracked probe (e.g., electromagnetically tracked or otherwise tracked) or imaging using on an x-ray device or other imaging modality, to obtain the locations of all points in a common coordinate system. This sampled data may be considered the "first positions" of the fiducials relative to one another. The primary transformation matrix $T_{tu}$ is then calculated between the tracker fiducials of tracker 107 and the transducer fiducials of scan head 110.

In an operation 403, the calibrated system may be used. This use may be in a clinical application or may include a test use. In any event, the initial calibration transformation $T_{ts}$ is employed to determine scan plane 106 of ultrasonic transducer 103 from sampled data of sensor elements 301 in tracker 107. As mentioned herein, this determination allows preoperative images such as CT images to be merged with interoperative ultrasound data. Operation 403 also includes removing tracker 107 from ultrasound device 100 and replacing tracker 107 in a different position relative to ultrasound transducer 103. In one embodiment, operation 403 need not involve removing tracker 107 from ultrasound device 100, but may include simply moving tracker 107 relative to scan head 110.

In an operation 404, tracker fiducials 203 on tracker 107 and the scan head fiducials 204 on scan head 110 are again sampled (e.g., using a tracked probe, imaging modality, or other method) in the same coordinate system and a secondary transformation matrix $T'_{tu}$ (which may be different from $T_{tu}$) is determined between scan head 110 and tracker 107. Here the prime (') in $T'_{tu}$ refers to a transformation occurring at a subsequent time from the unprimed value $T_{tu}$. These sampled data may be considered the "second positions" of the fiducials relative to one another.

In an operation 405, a differential transformation matrix T is calculated between $T_{tu}$ (the primary transformation) and $T'_{tu}$ (the secondary transformation). The differential transformation matrix T represents the difference between the first relative positions of tracker 107 and ultrasonic transducer 103 (the positions in which the initial calibration was calculated) and the second relative positions of tracker 107 and ultrasonic transducer 103. Because the relative positions between both 1) tracker fiducials 203 and sensor elements 301 and 2) scan head fiducials 204 and scan plane 206, are known and static, the difference between tracker fiducials 203 and scan head fiducials 204 (e.g., as represented by the differential transformation matrix T) provides an accurate representation of how to adjust the initial calibration. The transformation between the two coordinate systems is calculated as $T=T^{-1}_{tu} T'_{tu}$ where the "−1" superscript represents the inverse of the matrix.

In an operation 406, an adjusted calibration transformation matrix $T'_{ts}$ is calculated. Transformation matrix $T'_{ts}$ may be calculated by applying the differential transformation matrix T to the initial calibration transformation matrix $T_{ts}$. As mentioned above, this may also take into account the known and fixed positions of the tracker fiducials 203 to sensor elements 301, and the known and fixed positions of scan head fiducials 204 to scan plane 106. Essentially, scan plane 106 of ultrasonic transducer 103 is corrected by applying the differential transformation matrix T, so that scan plane 106 is known relative to tracker 107 in the new location/position. This enables the tracked coordinates of tracker 107 to be related to scan plane 106 of ultrasonic transducer 103 without having to perform a subsequent calibration step.

In an operation 407, trackable laparoscopic ultrasound device 100 may be used to merge preoperative images with interoperative ultrasound images using the tracked positions of tracker 107 and the adjusted calibration transformation matrix $T'_{ts}$, without re-calibrating the device. As such, wherever, tracker 107 is moved relative to ultrasonic transducer 103, only a differential fiducial transformation matrix need be calculated.

Figure 6:
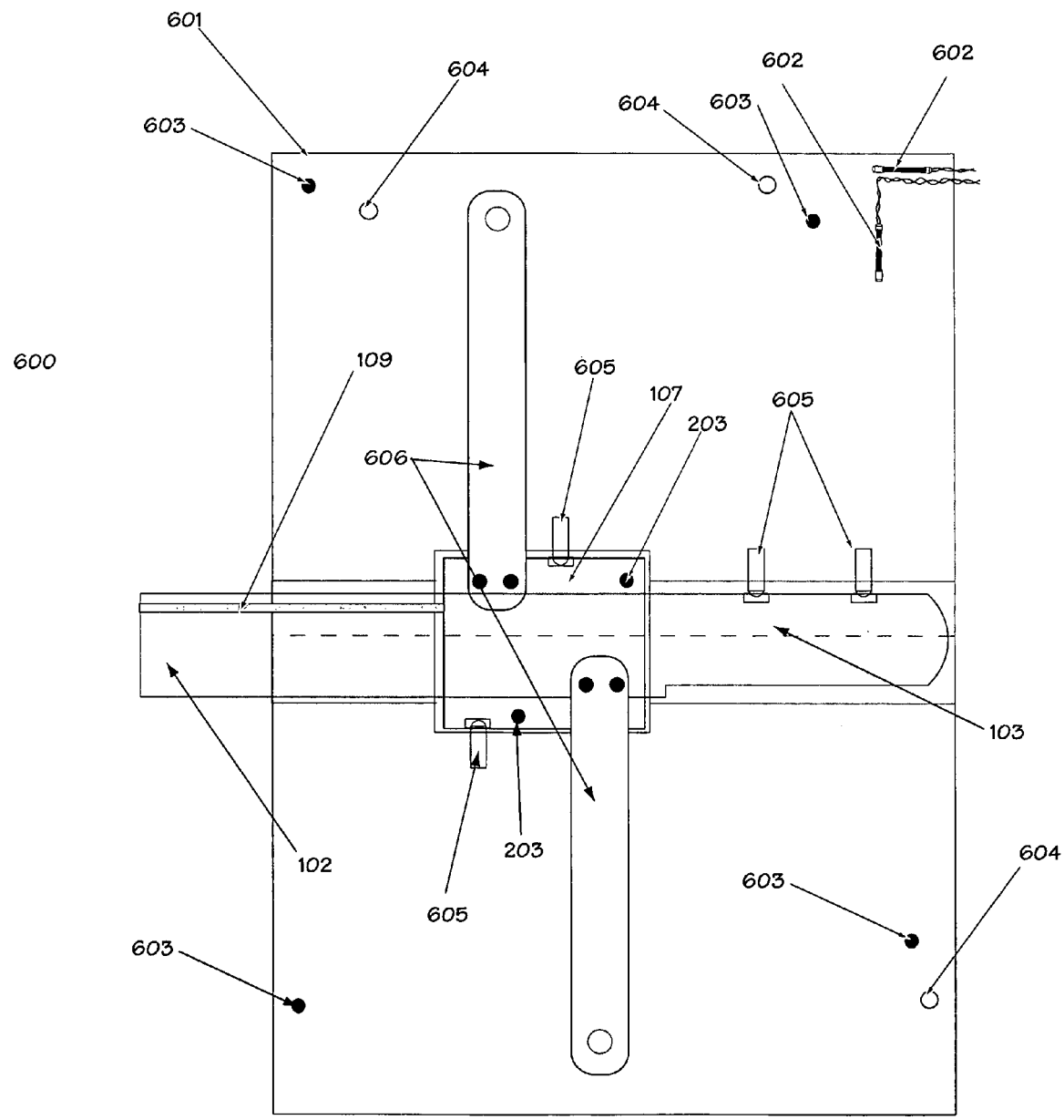
FIG. 6 illustrates a calibration jig in use with a trackable laparoscopic ultrasound device, according to an embodiment of the invention.

FIG. 6 illustrates an apparatus for use in determining the differential transformation matrix T that uses an embodiment of a calibration jig 600. Here, a block of material 601 (for example, a block of plastic) has been equipped with optional sensor elements 602 or other trackable elements. Fiducials 603 and/or digitization holes 604 suitable for determining the position of the block using a probe or x-ray in the coordinate space of the sensor elements 602 may also be present. All three of these elements (sensor elements 602, fiducials 603, digitization holes 604) may serve the same purpose since calibration jig 600 is manufactured to a known configuration. Calibration jig 600 may also contain alignment elements 605 that engage divots or other features on ultrasonic transducer 103 and/or tracker 107 (e.g., alignment elements 308, 309, or 501). Here alignment elements 605 are depicted as spring-loaded balls that "click into" divots on either tracker 107, ultrasonic transducer 103, or both, aligning and holding the elements in known locations and orientations.

Calibration jig 600 may also include outrigger elements 606 that assist in aligning tracker 107 with the ultrasonic transducer 103. The function of calibration jig 600 is, as above, to (1) assist in mechanically repositioning tracker 107 to the same location relative to ultrasonic transducer 103 and/or (2) enable the calculation of a new coordinate transformation of ultrasonic transducer relative to tracker 107. By knowing this relationship and the initial relationship between scan plan 106 and tracker 107, determination of tracker 107's location and orientation will provide enough information to accurately depict the location of scan plane 106 in any operation involving the combined device (i.e., ultrasound device 100). This will enable the location of scan plane 106 to be depicted on both CT and live ultrasound, for example.

Figure 7:
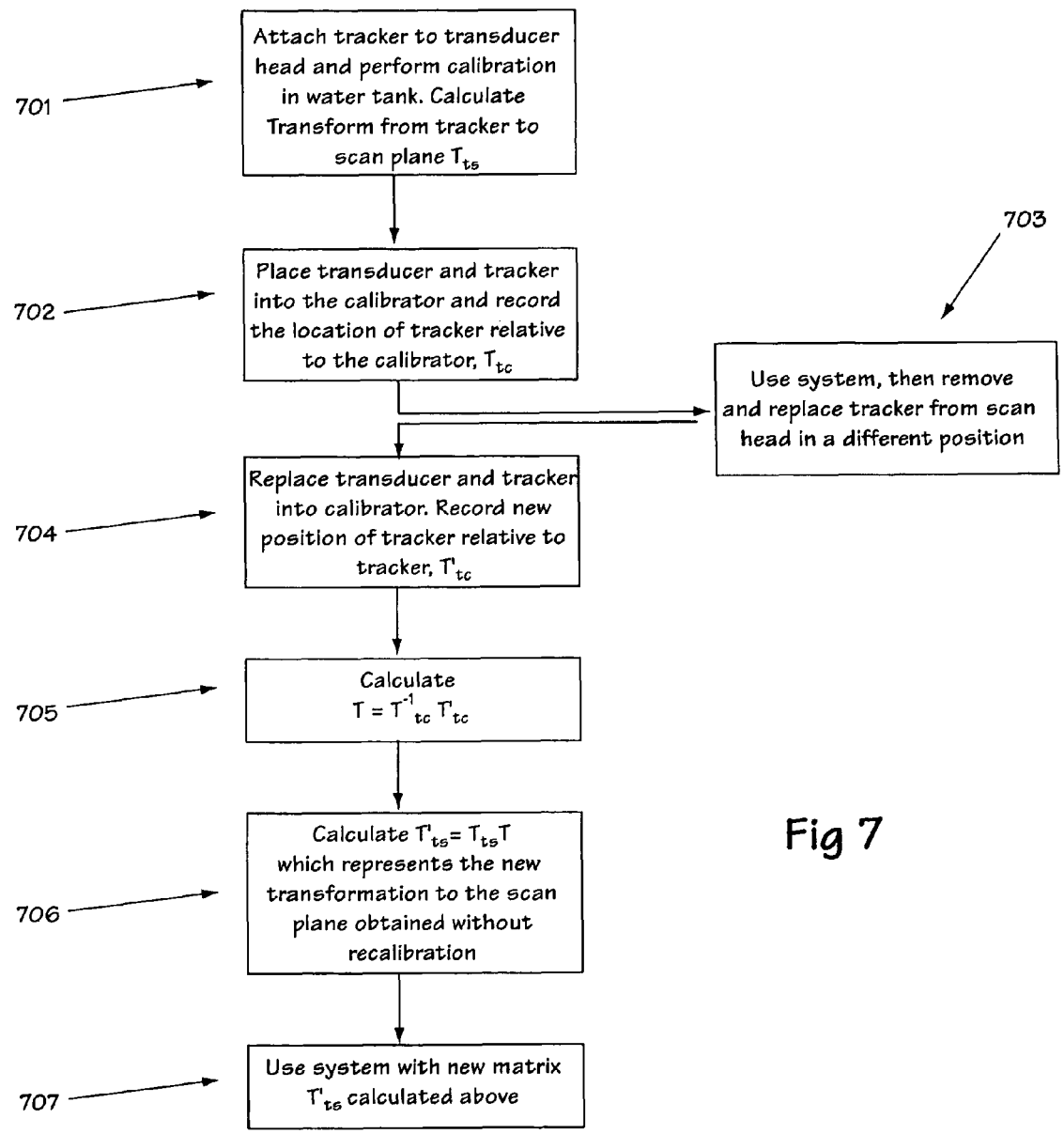
FIG. 7 illustrates a process for adjusting an initial calibration of a tracker to a scan plane in a trackable ultrasound device, according to an embodiment of the invention.

FIG. 7 illustrates a process 700 for performing a calibration using a jig such as, for example, calibration 600. Many of the operations of process 700 are analogous to those of process 400, illustrated in FIG. 4. In an operation 701, an initial calibration is performed similar to operation 401 of process 400, to determine an initial calibration transformation matrix $T_{ts}$.

In an operation 702, the combination of tracker 107 and ultrasonic transducer 103 is placed in calibration jig 600 and the location of tracker 107 relative to the calibration elements of calibration jig 600 (e.g., sensor elements 601, fiducials 603, digitization holes 604) is determined, taking care not to disturb the relative positions of tracker 107 and ultrasonic transducer 103. This may be done by measuring the location of tracker 107 using sensor elements 301 or tracking fiducials 203 on tracker 107 and then measuring the location of the sensor elements 602, fiducials 603, and/or digitization holes 604 on calibration jig 600. The position of tracker 107 relative to calibration jig 600 is used to determine a first calibration matrix $T_{tc}$, which may then be calculated using an ICP or SVD calculation as described in operation of 402 of process 400. Sampling of the fiducials in operation 702 may be performed using, for example, a tracked probe (e.g., electromagnetically tracked or otherwise tracked) or imaging the fiducials using on an x-ray device or other imaging modality, to obtain the locations of all points in a common coordinate system. Sampling of sensor elements 602 is performed using tracking device associated with the sensor elements such as an electromagnetic tracking device that may determine the locations and orientations of the sensor elements in a frame of reference.

In an operation 703, the calibrated system may be used. This use may be in a clinical application or may include a test use. In any event, the initial calibration transformation matrix $T_{ts}$ is employed to determine scan plane 106 of ultrasonic transducer 103 from sampled data of sensor elements 301 in tracker 107. As mentioned herein, this determination allows preoperative images such as CT, PET or MR images to be merged with intraoperative ultrasound data. Operation 703 also includes removing tracker 107 from ultrasound device 100 and replacing tracker 107 in a different position relative to ultrasound transducer 103. In one embodiment, operation 703 need not involve removing tracker 107 from ultrasound device 100, but may include simply moving tracker 107 relative to scan head 110.

In an operation 704, the combination of tracker 107 and ultrasound transducer 103 is returned to the calibration jig (having been removed for use in operation 703). Tracker fiducials 203 on tracker 107 and fiducials 603 or 604 of calibration jig 600 are again sampled (e.g., using a tracked probe, imaging modality, or other method) in the same coordinate system and a second transformation matrix $T'_{tc}$ (which may be different $T_{tc}$) from is determined between scan head 110 and tracker 107. Here the prime (') refers to a transformation occurring at a subsequent time. Alternately, the second matrix $T'_{tc}$ may be determined by sampling the sensor elements 301 in the tracker 107 and the sensor elements 602 in calibration jig 600.

In an operation 705, a differential transformation matrix T is calculated between $T_{tc}$ (the first transformation) and $T'_{tc}$ (the second transformation). The differential transformation matrix represents the difference between the first relative position of tracker 107 and ultrasonic transducer 103 (the positions in which the initial calibration was calculated) and the second relative positions of tracker 107 and ultrasonic transducer 103 (a subsequent location of the tracker, which may have been moved during use, cleaning or by accident). Because the relative positions between both 1) tracker fiducials 203 and sensor elements 301 and 2) scan head fiducials 204 and scan plane 206, are known and static, the difference between tracker fiducials 203 and scan head fiducials 204 (e.g., as represented by the differential transformation matrix) provides an accurate representation of how to adjust the initial calibration. The transformation between the two coordinate systems is calculated as $T=T^1_{tc} T'_{tc}$ where the "−1" superscript represents the inverse of the matrix.

In an operation 706, an adjusted calibration transformation matrix $T'_{ts}$ is calculated. Transformation matrix $T'_{ts}$ may be calculated by applying the differential transformation matrix T to the initial calibration transformation matrix $T_{ts}$. As mentioned above, this may also take into account the known and fixed positions of the tracker fiducials 203 to sensor elements 301, and the known and fixed positions of scan head fiducials 204 to scan plane 106. Essentially, scan plane 106 of ultrasonic transducer 103 is corrected by applying the differential fiducial transformation matrix T, so that scan plane 106 is known relative to tracker 107 in the new location/position. This enables the tracked coordinates of tracker 107 to be related to scan plane 106 of ultrasonic transducer 103 without having to perform a subsequent calibration step.

In an operation 707, trackable laparoscopic ultrasound device 100 may be used to merge preoperative images with interoperative ultrasound images using the tracked positions of tracker 107 and the adjusted calibration transformation matrix $T'_{ts}$, without re-calibrating the device. As such, wherever, tracker 107 is moved relative to ultrasonic transducer 103, only a differential fiducial transformation matrix need be calculated.

In some embodiments, more than one tracked ultrasound transducers can be used at one time. For example, a tracked ultrasound transducer can be used together with a second ultrasound transducer that provides increased and focused ultrasound energy for ablative treatment or pulsed focused ultrasound energy for assisted drug delivery. In these embodiments, the treatment ultrasound is tracked to the proper location and used to provide treatment, while the diagnostic ultrasound monitors the progress of the treatment, aids in navigation (e.g., by providing images), and may serve other purposes. In another embodiment, a single transducer may include both treatment (e.g., focused energy) and image capabilities. An example of a device capable of this dual use may be available from Focus Surgery™ of Indianapolis, Ind., U.S.A. In some embodiments, the diagnostic ultrasound can be replaced with an endoscope.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method of adjusting a calibration of a tracked ultrasound device, wherein the tracked ultrasound device includes a tracker and a scan head, wherein the tracker includes one or more tracker fiducial markings and one or more sensor elements, wherein the scan head has at least one scan plane originating therefrom and includes one or more scan head fiducial markings, the method comprising:
   attaching the tracker to the scan head in a first position;
   calculating an initial calibration transformation matrix that relates the one or more sensor elements to the at least one scan plane, such that the position and orientation of the one or more sensor elements enables determination of the position and orientation of the at least one scan plane;
   determining a first relative position of the one or more tracker fiducial markings in relation to the one or more scan head fiducial markings when the tracker is attached to the scan head in the first position;
   moving the tracker relative to the scan head into a second position;
   determining a second relative position of the one or more tracker fiducial markings in relation to the one or more scan head fiducial markings when the tracker is attached to the scan head in the second position;
   calculating a difference between the first and second relative positions of the tracker fiducial markings and the scan head fiducial markings; and
   adjusting the initial calibration transformation matrix using the calculated difference between the first and second relative positions of the tracker fiducial markings and the scan head fiducial markings.

2. The method of claim 1, wherein the one or more sensor elements include one or more electromagnetic sensor elements, and wherein the method further comprises determining a position and orientation of the one or more electromagnetic sensor elements using an electromagnetic tracking device.

3. The method of claim 1, wherein calculating the initial calibration transformation matrix includes calculating the initial calibration transformation matrix that relates to one or more of inertial guidance sensors, ultrasonic sensors, optical sensors, or fiber optic sensors.

4. The method of claim 1, wherein determining a first relative position of the one or more tracker fiducial markings in relation to the one or more scan head fiducial markings further comprises sampling first positions of the one or more tracker fiducial markings and the one or more scan head fiducial markings in the same frame of reference, and wherein determining a second relative position of the one or more tracker fiducial markings in relation to the one or more scan head fiducial markings further comprises sampling second positions of the one or more tracker fiducial markings and the one or more scan head fiducial markings in the same frame of reference.

5. The method of claim 4, wherein sampling positions of the one or more tracker fiducial markings and the one or more scan head fiducial markings in the same frame of reference further comprises touching a tracked probe to each of the one or more tracker fiducial markings and each of the one or more scan head fiducial markings.

6. The method of claim 4, wherein sampling positions of the one or more tracker fiducial markings and the one or more scan head fiducial markings in the same frame of reference further comprises imaging the one or more tracker fiducial markings and the one or more scan head fiducial markings with an imaging modality.

7. The method of claim 4, wherein sampling positions of the one or more tracer fiducial markings comprises measuring a location of the one or more sensor elements whose positions are known relative to the tracker fiducial markings.

8. The method of claim 1, wherein determining a first relative position of the one or more tracker fiducial markings in relation to the one or more scan head fiducial markings further comprises:
   i) placing the tracker and the scan head into a calibration jig when the tracker is attached to the scan head in the first position, and
   ii) determining the relative position of the one or more tracker fiducial markings to one or more calibration jig fiducial markings,
wherein determining a second relative position of the one or more tracker fiducial markings in relation to the one or more scan head fiducial markings further comprises:
   i) placing the tracker and the scan head into the calibration jig when the tracker is attached to the scan head in the second position, and
   ii) determining the relative position of the one or more tracker fiducial markings to the one or more calibration jig fiducial markings,
and wherein a relative position of the one or more scan head fiducial markings and the one or more calibration jig fiducial markings remains the same in the first and second positions.

9. The method of claim 1, wherein determining a first relative position of the one or more tracker fiducial markings in relation to the one or more scan head fiducial markings further comprises calculating a primary transformation matrix that relates the one or more tracker fiducial markings to the one or more scan head fiducial markings in the first position,
and wherein determining a second relative position of the one or more tracker fiducial markings in relation to the one or more scan head fiducial markings further comprises calculating a secondary transformation matrix that relates the one or more tracker fiducial markings to the one or more scan head fiducial markings in the second position.

10. The method of claim 9, wherein calculating a difference between the first and second relative positions of the tracker fiducial markings and the scan head fiducial markings further includes calculating a differential transformation matrix.

11. The method of claim 10, wherein adjusting the initial calibration transformation matrix further comprises applying the differential transformation matrix to the initial calibration transformation matrix.

12. A method for repeatable replacement of a tracker onto an ultrasound device, wherein the tracker includes at least one sensor element and one or more tracker alignment elements, wherein the ultrasound device includes a scan head and one or more scan head alignment elements, wherein at least one scan plane originates from the scan head, and wherein each of the one or more tracker alignment elements corresponds to one of the one or more scan head alignment elements, the method comprising:
   calibrating the at least one scan plane to the at least one sensor element when the tracker is attached to the scan head in a first position, such that the position and orientation of the at least one scan plane is determinable from the position and orientation of the at least one sensor element;
   removing the tracker from the scan head;
   re-attaching the tracker to the scan head;
   placing the tracker and the scan head into a calibration jig that includes one or more calibration jig alignment elements that each correspond to at least one tracker alignment element or scan head alignment element and
   aligning each of the one or more calibration jig alignment elements to its corresponding tracker alignment element or scan head alignment element causing the tracker to be aligned onto the scan head in the first position.

13. The method of claim 12, wherein placing the tracker and the scan head into the calibration jig includes placing each of the tracker and the scan head into a calibration jig that includes one or more calibration jig alignment elements that each correspond to one or more of:
   spring loaded balls and corresponding divots,
   pegs and corresponding holes,
   clips and corresponding clip receiving divots,
   mechanical alignment guides,
   corresponding markings, or
   matable grooves.

14. The method of claim 12, wherein the at least one sensor element is an electromagnetic sensor element, and wherein the method further comprises determining a position and orientation of the electromagnetic sensor element using an electromagnetic tracking device.

* * * * *